(12) United States Patent
Barkalow et al.

(10) Patent No.: US 7,214,807 B2
(45) Date of Patent: May 8, 2007

(54) METHOD FOR THE PREPARATION OF FLUTICASONE AND RELATED 17β-CARBOTHIOIC ESTERS USING A NOVEL CARBOTHIOIC ACID SYNTHESIS AND NOVEL PURIFICATION METHODS

(75) Inventors: Jufang Barkalow, Deerfield, IL (US); Steven A. Chamberlin, Waukegan, IL (US); Arthur J. Cooper, Lake Villa, IL (US); Azad Hossain, Lindenhurst, IL (US); John J. Hufnagel, Lake Villa, IL (US); Denton Langridge, Wildwood, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/847,846

(22) Filed: May 18, 2004

(65) Prior Publication Data
US 2004/0209854 A1    Oct. 21, 2004

Related U.S. Application Data

(63) Continuation of application No. 09/513,399, filed on Feb. 25, 2000.

(51) Int. Cl.
*C07J 31/00*    (2006.01)
*C07J 7/00*    (2006.01)

(52) U.S. Cl. ...................................... 552/569; 552/559
(58) Field of Classification Search ................ 552/220, 552/559; 514/178, 179, 172
See application file for complete search history.

(56) References Cited

U.S. PATENT DOCUMENTS

| | | | |
|---|---|---|---|
| 4,188,385 A | 2/1980 | Edwards | |
| 4,198,403 A | 4/1980 | Alvarez | |
| 4,263,289 A * | 4/1981 | Edwards | 514/179 |
| 4,335,121 A | 6/1982 | Phillipps et al. | |
| 4,578,221 A | 3/1986 | Phillipps et al. | |
| 6,406,718 B1 * | 6/2002 | Cooper | 424/489 |
| 6,747,163 B2 * | 6/2004 | Rubinsztain et al. | 552/220 |

FOREIGN PATENT DOCUMENTS

| | | |
|---|---|---|
| GB | 2088877 | 6/1982 |
| GB | 2137206 | 10/1984 |
| IL | 109656 | 1/1998 |

OTHER PUBLICATIONS

Phillipps et al, J. Med. Chem. 1994, 37, 3717-3729.*
Karteez et al. (DN 105:6673, HCAPLUS, J. of Organic Chemistry (1986), 51(12), 2315-28).*
Journal of Medicinal Chemistry, vol. 37, No. 22 1994, pp. 1276-1278.
Journal of Organic Chemistry, vol. 23, No. 8, 1958, p. 1277.
Journal of The American Chemical Society, vol. 108 No. 3, 1986, pp. 452-461.
Journal of The Chemical Society, Chemical Communications, No. 19, 1989, pp. 1435-1436.
Bull. Chem. Soc. Jpn 50(11):3071 (1977).
J. Ind. Chem. Soc. 52:150 (1977).
J. Org. Chem. 31:3980 (1966).
Org. Syn. Collective vol. VI:824 (1988).
J. Am. Chem. Soc. 69:2682 (1947).
Synlett. 11:1054 (1996).
J. Med. Chem. 37(22):3171 (1994).
J. Org. Chem. 51(12):2315 (1986).
Tetrahedron 36(4):539 (1980).
Chem. Ber. 113(5):1898 (1980).
Justus Liebigs Ann. Chem. 590:123 (1954).

* cited by examiner

*Primary Examiner*—Sabiha N. Qazi
(74) *Attorney, Agent, or Firm*—Johanna M Corbin

(57) ABSTRACT

This invention discloses a novel method for the conversion of carboxylic acids to carbothioic acids and application of the method to the preparation of androstane carbothiolates, such as fluticasone propionate, which avoids column chromatography.

7 Claims, No Drawings

METHOD FOR THE PREPARATION OF FLUTICASONE AND RELATED 17β-CARBOTHIOIC ESTERS USING A NOVEL CARBOTHIOIC ACID SYNTHESIS AND NOVEL PURIFICATION METHODS

This application is a continuation of U.S. patent application Ser. No. 09/513,399, filed Feb. 25, 2000.

TECHNICAL FIELD

This invention relates to a novel method for the conversion of carboxylic acids to carbothioic acids, use of the method for the preparation of androstane 17β-carbothioic acids, and methods for the preparation of fluticasone propionate.

BACKGROUND OF THE INVENTION

Fluticasone propionate belongs to a class of androstane 17β-carbothioic esters which are well-known in the art as antiinflammatories. Because of the therapeutic usefulness of these compounds, there is sustained interest in improving the synthesis of androstane 17β-carbothioic esters in general, and fluticasone propionate in particular.

Prior art such as U.S. Pat. Nos. 4,188,385, 4,198,403, 4,335,121, and 4,578,221; British patents 2,088,877 and 2,137,206; and published Israeli patent application IL 109,656-A1 teach the synthesis of fluticasone propionate from commercial grade flumethasone. These syntheses involve complicating factors such as chromatography of intermediates, low-yielding steps, and high pressure addition of chlorofluoromethane.

Commercial grade flumethasone ((6α, 11β, 16α)-6,9-difluoro-11,17,21-trihydroxy-16-methylpregna-1,4-diene-3,20-dione) typically contains from about 0.5% to 2% of (6α,11β,16α)-6-chloro-9-fluoro-11,17,21-trihydroxy-16-methylpregna-1,4-diene-3,20-dione as an impurity (hereinafter referred to as the Cl impurity), the removal of which is achieved by column chromatography, a method not amenable to large scale manufacture.

Conversion of the 17β-carboxylic acid of 6α,9α-difluoro-11 β-hydroxy-16α-methyl-3-oxo-17α-(propionyloxy)androsta-1,4-diene-17β-carboxylic acid to a carbothioic acid is also problematic. General methods for the conversion of carboxylic acids to carbothioic acids include reaction of activated carboxylic acids and a sulfide source (*Advanced Organic Chemistry. Reactions, Mechanisms, and Structure,* 4th ed., John Wiley & Sons, New York, 1992; and U.S. Pat. No. 4,578,221) and application of thiocarbamate hydrolysis chemistry to thiocarbamylanhydrides (*Bull. Chem. Soc. Jpn.,* 1977, 50(11), 3071; *J. Ind. Chem. Soc.,* 1977, 52, 150; *J. Org. Chem.,* 1966, 31, 3980; *Org. Syn.,* 1988, Collective Volume VI, 824; *J. Am. Chem. Soc.* 1947, 69, 2682; and *Synlett.,* 1996, 11, 1054). Use of these methods in the synthesis of fluticasone propionate, however, provide only modest yields due to incompatibility of the reaction conditions with other groups on the molecule (*J. Med. Chem.,* 1984, 37(22) 3171 and *J. Org. Chem.* 1986, 51(12) 2315).

Direct conversion of the carbothioic acid group of androstane 17β-carbothioic acids to a carbothiolate esters is achieved by reaction of the carbothioic acids, chlorofluoromethane, and base at high pressures, another method which is not amenable to large scale manufacture.

Thus, there is a continuing need in the pharmaceutical manufacturing industry for an efficient method for the conversion of carboxylic acids to carbothioic acid esters which is applicable to the large scale conversion of androstane 17β-carboxylic acids to androstane 17β-carbothioic esters in general and fluticasone propionate, in particular.

SUMMARY OF THE INVENTION

In one embodiment of this invention is disclosed a method for converting carboxylic acid groups to carbothioic acid groups comprising:
(a) reacting a compound having the carboxylic group and a first base, an iodide salt, and a compound of formula (4)

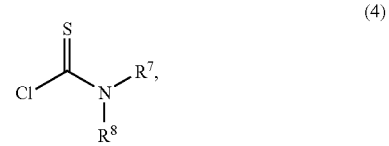

(4)

wherein $R^7$ and $R^8$ are independently $C_1$–$C_6$ alkyl; or $R^7$ and $R^8$ together are $C_1$–$C_6$ alkylene;
(b) reacting the product of step (a) and a hydrolyzing agent; and
(c) reacting the product from step (b) and acid.

In a preferred embodiment of the above method directly above is disclosed a method for the conversion of a carboxylic acid group to a carbothioic acid group, the method comprising:
(a) reacting a compound having the carboxylic acid group and a first base, an iodide salt, and N,N-dimethylthiocarbamoyl chloride at about 10° C. to about 30° C. in a solvent system comprising an organic component and water, the water present in about one quarter percent by weight to about ten percent by weight of the compound having the carboxylic acid group;
(b) reacting the product from step (a) and an alkoxide salt, a thioalkoxide salt, an optionally hydrated sulfide salt, or a mixture thereof at about −40° C. to about 35° C.; and
(c) reacting the product from step (b) and acid.

In another embodiment of this invention is disclosed a method for dehalogenating a 4-halo-2,3-unsaturated carbonyl group comprising reacting a compound having the 4-halo-2,3-unsaturated carbonyl group, a palladium catalyst, and an additive, optionally in the presence of a reducing agent.

In another embodiment of this invention is disclosed a method for the preparation of a compound of formula (7)

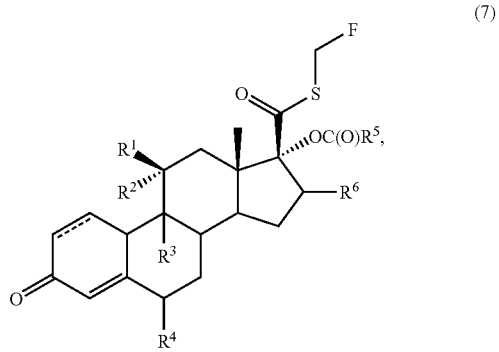

(7)

wherein the ----- symbol represents a single bond or a double bond; one of $R^1$ or $R^2$ is hydrogen and the other is optionally protected hydroxyl; or $R^1$ and $R^2$ together are oxo; $R^3$ and $R^4$ are independently hydrogen or halide; and $R^5$ and $R^6$ are independently $C_1$–$C_6$ alkyl;

the method comprising:

(a) reacting a compound of formula (1)

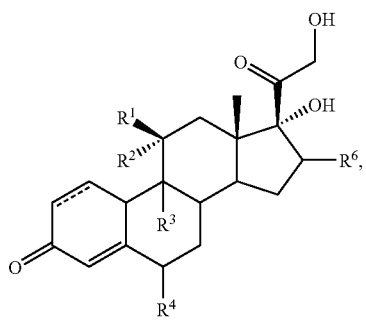

(1)

and periodic acid to provide a compound of formula (2)

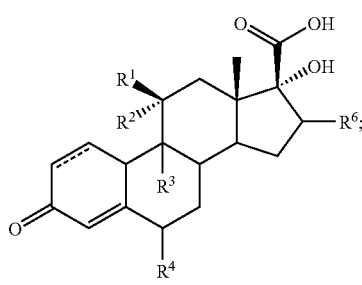

(2)

(b) reacting the product of step (a) and an alkanoyl halide and the first base to provide a compound of formula (3)

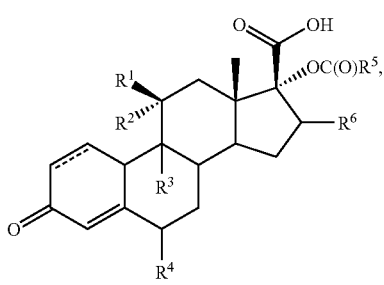

(3)

(c) reacting the product of step (b) and a first base, an iodide salt, and the compound of formula (4) to provide a compound of formula (5)

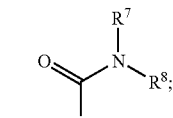

(5)

(d) reacting the product of step (c) and a hydrolyzing agent to provide a compound of formula (6)

(6)

wherein M is Li, Na, or K;

(e) optionally reacting the product of step (d) and acid;

(f) reacting the product of step (e) and chlorofluoromethane optionally in the presence of a second base; and (g) optionally deprotecting the product of step (f).

In a preferred embodiment of the method directly above, the compound of formula (1) is commercial grade flumethasone;

the compound of formula (2) is 6α,9α-difluoro-11β,17α-dihydroxy-16α-methyl-3-oxoandrosta-1,4-diene-17β-carboxylic acid;

the compound of formula (3) is 6α,9α-difluoro-11β-hydroxy-16α-methyl-3-oxo-17α-(propionyloxy)androsta-1,4-diene-17β-carboxylic acid;

the compound of formula (5) is 17β-(N,N-(dimethylcarbamoyl)thio)carbonyl-6α,9α-difluoro-11β-hydroxy-16α-methyl-17α-propionyloxy-3-oxoandrosta-1,4-diene; and the compound of formula (7) is 6α,9α-difluoro-17α-(((fluoromethyl)sulfanyl)-carbonyl)-11β-hydroxy-16α-methyl-3-oxoandrosta-1,4-dien-17α-yl propionate.

In another embodiment of this invention is disclosed a method for the purification of 6α,9α-difluoro-11β-hydroxy-16α-methyl-3-oxo-17α-(propionyloxy)androsta-1,4-diene-17β-carboxylic acid by recrystallization.

In another embodiment of this invention is disclosed a method for the purification of 6α,9α-difluoro-11β-hydroxy-16α-methyl-3-oxo-17α-(propionyloxy)androsta-1,4-diene-17βcarboxylic acid by repeated recrystallization.

In another embodiment of this invention is disclosed a method for the purification of the compound formula (1), the compound of formula (2), the compound of formula (3), the compound of formula (5), or the compound of formula (7) by treatment with a palladium catalyst and an additive, optionally in the presence of a reducing agent.

In another embodiment of this invention is disclosed an improved method for the preparation of 6α,9α-difluoro-17β-(((fluoromethyl)sulfanyl)carbonyl)-11β-hydroxy-16α-methyl-3-oxoandrosta-1,4-dien-17α-yl propionate (fluticasone propionate) which omits the use of column chromatography and is applicable to large scale.

In another embodiment of this invention is disclosed a method for the removal of the Cl impurity in the synthesis of fluticasone propionate using a palladium catalyst and an additive, optionally in the presence of a reducing agent.

In another embodiment of this invention is disclosed a method for the removal of the Cl impurity from commercial grade flumethasone using a palladium catalyst and an additive, optionally in the presence of a reducing agent.

DETAILED DESCRIPTION OF THE INVENTION

This invention discloses a novel method for the conversion of carboxylic acids to carbothioic acids and application of the method to the preparation of androstane carbothiolates, such as fluticasone propionate, which avoids column chromatography.

Definition of Terms

The term "acid," as used herein, refers to reagents capable of donating protons during the course of a chemical reaction. Examples of acids include mineral acids such as hydrofluoric, hydrochloric, hydrobromic, hydroiodic, sulfuric, phosphoric, and the like; organic acids such as formic, acetic, propionic, trifluoroacetic, and the like; and sulfonic acids such as para-toluenesulfonic, para-bromosulfonic, para-nitrosulfonic, and the like. The acid chosen for a particular conversion depends on the nature of the starting materials, the solvent or solvents in which the reaction is conducted, and the temperature at which the reaction is conducted.

The term "additive," as used herein, refers to monodentate phosphorus-containing ligands of formulas $P(R^C)_3$ (phosphines) and $P(OR^D)_3$ (phosphites), wherein each $R^C$ is independently hydrogen; $C_1-C_6$ alkyl such as methyl, ethyl, and tert-butyl; cycloalkyl such as cyclopropyl and cyclohexyl; optionally substituted aryl such as phenyl, naphthyl, and ortho-tolyl; and optionally substituted heteroaryl such as furyl and pyridyl; and wherein each $R^D$ is independently $C_1-C_6$ alkyl such as methyl, ethyl, and tert-butyl; cycloalkyl such as cyclopropyl and cyclohexyl; optionally substituted aryl such as phenyl, naphthyl, and ortho-tolyl; and optionally substituted heteroaryl such as furyl and pyridyl. Specific examples of these additives include tri(alkyl)phosphines such as trimethylphosphine, triethylphosphine, tributylphosphine, and the like; tri(cycloalkyl)phosphines such as tricyclopropylphosphine, tricyclohexylphosphine, and the like; tri(aryl)phosphines such as triphenylphosphine, trinaphthylphosphine, and the like; tri(heteroaryl)phosphines such as tri(fury-2-yl)phosphine, tri(pyrid-3-yl)phosphine, and the like; tri(alkyl)phosphites such as trimethylphosphite, triethylphosphite, tributylphosphite, and the like; tri(cycloalkyl)phosphites such as tricyclopropylphosphite, tricyclohexylphosphite, and the like; tri(aryl)phosphites such as triphenylphosphite, trinaphthylphosphite, and the like; and tri(heteroaryl)phosphites such as tri(fury-2-yl)phosphite, tri (pyrid-3-yl)phosphite, and the like. The term "additive," as used herein, also refers to bidentate phosphines such as 1,4-bis(diphenylphosphino)butane (dppb), 1,2-bis(diphenylphosphino)ethane (dppe), 1,1-bis(diphenylphosphino)methane (dppm), 1,2-bis(dimethyl-phosphino)ethane (dmpe), 1,1'-bis(diphenylphosphino)ferrocene (dppf), and the like.

The term "alkali metal iodide," as used herein, refers to lithium iodide, sodium iodide, potassium iodide, cesium iodide, and the like.

The term "alkali earth metal iodides," as used herein, refers to magnesium iodide, calcium iodide, barium iodide, and the like.

The term "alkanoyl halide," as used herein, refers to $R^AC(O)X$, wherein $R^A$ is $C_1-C_6$ alkyl, and X is chloride or bromide.

The term "$C_2-C_6$ alkenyl," as used herein, refers to a straight or branched chain hydrocarbon radical having from 2 to 6 carbons and at least one carbon-carbon double bond.

The term "alkoxide salt," as used herein, refers to $[M]^+ [OR^A]^-$, wherein M is Li, Na, or K, and $R^A$ is $C_1-C_6$ alkyl.

The term "alkoxy," as used herein, refers to an alkyl group attached to the parent molecular group through an oxygen atom.

The terms "$C_1-C_6$ alkyl," as used herein, refers to a straight or branched chain saturated hydrocarbon radical having from 1 to 6 carbons.

The term "$C_1-C_6$ alkylene," as used herein, refers to a straight or branched chain saturated hydrocarbon diradical having from 1 to 6 carbons.

The term "amino," as used herein, refers to $-NH_2$ or a derivative thereof formed by replacement of a hydrogen atom thereon or independent replacement of both hydrogen atoms thereon by an alkyl, cycloalkyl, cycloalkylalkyl, or arylalkyl group.

The term "aryl," as used herein, refers to a cyclic, aromatic carbocyclic ring such as phenyl or two fused aromatic carbocyclic rings such as naphthyl. The aryl groups of this invention can be optionally independently substituted with one, two, or three alkyl, amino, halo, and nitro substituents. The aryl groups of this invention can be optionally independently substituted with one, two, three, four, or five $C_1-C_6$ alkyl, $C_2-C_6$ alkenyl, halo, carboxyl, carboxaldehyde, alkoxycarbonyl, $C_1-C_6$ perfluoroalkyl, or nitro substituents.

The term "arylalkyl," as used herein refers to an aryl group attached to the parent molecular group through an alkyl group.

The term "borane," as used herein, refers to compounds containing at least one boron-hydrogen bond and are exemplified by diborane, 9-borabicyclo[3.3.1]nonane (9-BBN), dilongifoylborane, thexylborane, catecholborane, sodium borohydride, tetrabutylammonium borohydride, borane-4-methylmorpholine complex, borane-4-ethylmorpholine complex, borane-dimethylsulfide complex, borane-triethylamine complex, borane-pyridine complex, borane-2,6-lutidine complex, and the like.

The term "carbonate salt," as used herein, refers to lithium carbonate, lithium bicarbonate, sodium carbonate, sodium bicarbonate, potassium carbonate, potassium bicarbonate, cesium carbonate, and the like.

The term "carbothioic acid," as used herein, refers to $-C(O)SH$.

The terms "carboxylic acid" and "carboxyl," as used herein, refer to —C(O)OH.

The term "carboxaldehyde," as used herein, refers to —CHO.

The term "commercial grade flumethasone," as used herein, refers to (6α,11β,16α)-6,9-difluoro-11,17,21-trihydroxy-16-methylpregna-1,4-diene-3,20-dione containing up to 2% of (6α, 11β, 16α)-6-chloro-9-fluoro-11,17,21-trihydroxy-16-methylpregna-1,4-diene-3,20-dione as an impurity.

The term "cycloalkyl," as used herein refers to a saturated, cyclic hydrocarbon group having three to six carbon atoms.

The term "cycloalkylalkyl," as used herein refers to a cycloalkyl group attached to the parent molecular group through an alkyl group.

The term "dehalogenating," as used herein, refers to the removal of a chloride bromide, or iodide radical of a 4-halo-2,3-unsaturated carbonyl group.

The terms "first base," and "second base," as used herein, refer to reagents capable of accepting protons during the course of a chemical reaction. Examples of first and second bases include carbonates such as lithium carbonate, lithium bicarbonate, sodium carbonate, sodium bicarbonate, potassium carbonate, potassium bicarbonate, cesium carbonate, and the like; phosphates such as potassium phosphate, potassium hydrogen phosphate, potassium dihydrogen phosphate, and the like; trialkylamines such as triethylamine, diisopropylethylamine, and the like; heterocyclic amines such as imidazole, pyridine, pyridazine, pyrimidine, pyrazine, and the like; and bicyclic amines such as DBN, DBU, and the like. The base chosen for a particular conversion depends on the nature of the starting materials, the solvent or solvents in which the reaction is conducted, and the temperature at which the reaction is conducted.

The terms "halide" and "halo," as used herein, refer to F, Cl, Br, and I.

The term "4-halo-2,3-unsaturated carbonyl," as used herein, refers to a endogenous or exogenous group comprising at least four carbon atoms, wherein carbon-1 is substituted with oxo, carbon-2 and carbon-3 are connected by a carbon-carbon double bond, and carbon-4 bears a chloride, bromide, or iodide substituent.

The term "heteroaryl," as used herein, refers to aromatic rings having five or six atoms, wherein at least one of the atoms is nitrogen, oxygen, or sulfur and the remainder are carbon. The five-membered rings have two double bonds, and the six-membered rings have three double bonds. The heteroaryls of this invention are connected to the phosphorus atom through a carbon atom in the ring. The heteroaryl groups of this invention can be optionally independently substituted with one, two, or three $C_1$–$C_6$ alkyl, $C_2$–$C_6$ alkenyl, halo, carboxyl, carboxaldehyde, alkoxycarbonyl, $C_1$–$C_6$ perfluoroalkyl, or nitro substituents.

The term "hydroxyl," as used herein, refers to —OH.

The term "hydroxyl protecting group," as used herein, refers to selectively introducible and removable groups which protect hydroxyl groups against undesirable side reactions during synthetic procedures. Examples of hydroxyl protecting groups include benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl, para-methoxybenzyl, 3,4-dimethoxybenzyl, diphenylmethyl, triphenylmethyl, tetrahydrofuryl, tetrahydropyranyl, tetrahydrothiopyranyl. methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl; alkylsulfonyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "nitro," as used herein, refers to —$NO_2$.

The term "organic component," as used herein, refers to a solvent which is not reactive with the starting materials and in which the starting materials are at least partially soluble. Examples of organic components include, $C_2$–$C_5$ alkylamides such as formamide, N,N-dimethylformamide, N,N-dimethylacetamide, and the like; $C_4$–$C_6$ dialkoxyalkyls as DME, 1,2-diethoxyethane, and the like; $C_1$–$C_4$ alcohols such as methanol, ethanol, propanol, iso-propanol, butanol, iso-butanol, sec-butanol, tert-butanol, and the like; $C_3$–$C_{10}$ ketones such as acetone, 2-butanone, 3-pentanone, 2-butanone, 2-pentanone, 2,5-heptanedione, and the like; $C_5$–$C_7$ hydrocarbons such as pentane, hexane, heptane, and the like; optionally substituted aromatic hydrocarbons such as benzene, toluene, 1,4-dichlorobenzene, nitrobenzene, and the like; ethers such as diethyl ether, diisopropyl ether, and the like; and esters such as ethyl acetate isopropyl acetate, and the like.

The term "oxo," as used herein, refers to a group formed by the replacement of two hydrogen atoms on the same carbon atom with a single oxygen atom.

The term "palladium catalyst," as used herein, refers to optionally supported palladium such as palladium metal, palladium metal on carbon, and palladium metal on acidic, basic, or neutral alumina; palladium(0) complexes such as tetrakis(triphenylphosphine)palladium(0); palladium salts such as palladium(II) acetate or palladium(II) chloride; and palladium(II) complexes such as allylpalladium(II) chloride dimer, (1,1'-bis(diphenylphosphino)ferrocene)-dichloropalladium(II), bis(acetato)bis(triphenylphosphine)palladium (II), and bis(acetonitrile)dichloropalladium(II).

The term "$C_1$–$C_6$ perfluoroalkyl," as used herein, refers to a $C_1$–$C_6$ alkyl group, wherein all of the hydrogen radicals have been replaced by fluoride radicals.

The term "protected hydroxyl," as used herein, refers to a hydroxyl to which is attached a hydroxyl protecting group.

The term "reducing agent," as used herein, refers to boranes, silanes and stannes.

The term "silane," as used herein, refers to $Si(R^E)(R^F)_3$, wherein $R^E$ is hydrogen, and each $R^F$ is independently hydrogen, $C_1$–$C_{20}$ alkyl, $C_2$–$C_{20}$ alkenyl, aryl, or heteroaryl. Specific examples of silanes include diethylsilane, dimethylisopropylsilane, tributylsilane, cyclohexyldimethylsilane, diisopropyloctylsilane, triisopropylsilane, dimethylethylsilane, dimethyloctadecylsilane, triethylsilane, and the like.

The term "stannane," as used herein, refers to $Sn(R^E)(R^F)_3$, wherein $R^E$ is hydrogen, and each $R^F$ is independently hydrogen, $C_1$–$C_{20}$ alkyl, $C_2$–$C_{20}$ alkenyl, aryl, or heteroaryl. Specific examples of stannanes include diethylstannane, dimethylisopropylstannane, tributylstannane, cyclohexyldimethylstannane, diisopropyloctylstannane, triisopropylstannane, dimethylethylstannane, dimethyloctadecylstannane, triethylstannane, and the like.

The term "sulfide salt," as used herein, refers to lithium sulfide, lithium hydrosulfide, sodium sulfide, sodium hydrosulfide, potassium sulfide, potassium hydrosulfide, and the like. The sulfide salts of this invention can be optionally hydrated.

The term "hydrolyzing agent," as used herein, refers to alkoxide salts, thioalkoxide salts, optionally hydrated sulfide salts, and mixtures thereof.

The term "iodide salt," as used herein, refers to alkali metal iodides, alkali earth metal iodides, and tetraalkylammonium iodides.

The term "tetraalkylammonium iodide," as used herein, refers to compounds of formula $[(R^B)_4N]^+[I]^-$, wherein $R^B$ is $C_1$–$C_{20}$ alkyl.

The term "thioalkoxide salt," as used herein, refers to $[M]^+[SR^A]^-$, wherein M is Li, Na, or K, and $R^A$ is $C_1$–$C_6$ alkyl.

Asymmetric centers exist in the compounds of this invention. This invention contemplates stereoisomers and mixtures thereof. Individual stereoisomers of compounds are prepared by synthesis from starting materials containing the chiral centers or by preparation of mixtures of enantiomeric products followed by separation such as conversion to a mixture of diastereomers followed by separation or recrystallization, chromatographic techniques, or direct separation of the enantiomers on chiral chromatographic columns. Starting compounds of particular stereochemistry are either commercially available or are made by the methods described herein and resolved by techniques well-known in the art.

Percentages such as mole % and % Cl impurity were obtained by HPLC analyses of starting materials and products. Values were calculated from the the peak area.

All of the processes of this invention can be conducted as continuous processes. The term "continuous process," as used herein, refers to the conduction of a reaction to provide an intermediate followed by use, optionally in situ, of the intermediate, without isolation, in a subsequent reaction. The term "in situ," as used herein, refers to use of an intermediate in the solvent in which the intermediate was prepared without removal of the solvent.

Abbreviations

Abbreviations which have been used are: DBN for 1,5-diazobicyclo[4.3.0]non-5-ene; DBU for 1,8-diazobicyclo[5.4.0]undec-7-ene; DBA for dibenzylidine acetone; DMA for N,N-dimethylacetamide; DME for dimethoxyethane; DMF for N,N-dimethylformamide; HPLC for high pressure liquid chromatography; and THF for tetrahydrofuran.

Synthetic Methods

The methods of this invention will be better understood in connection with the following synthetic scheme which illustrates an embodiment of this invention. It will be readily apparent to one of ordinary skill in the art that the compounds of this invention can be prepared by substitution of the appropriate reactants and agents in the synthesis shown below. It will also be apparent to one skilled in the art that the order of the steps themselves can be varied.

Scheme 1

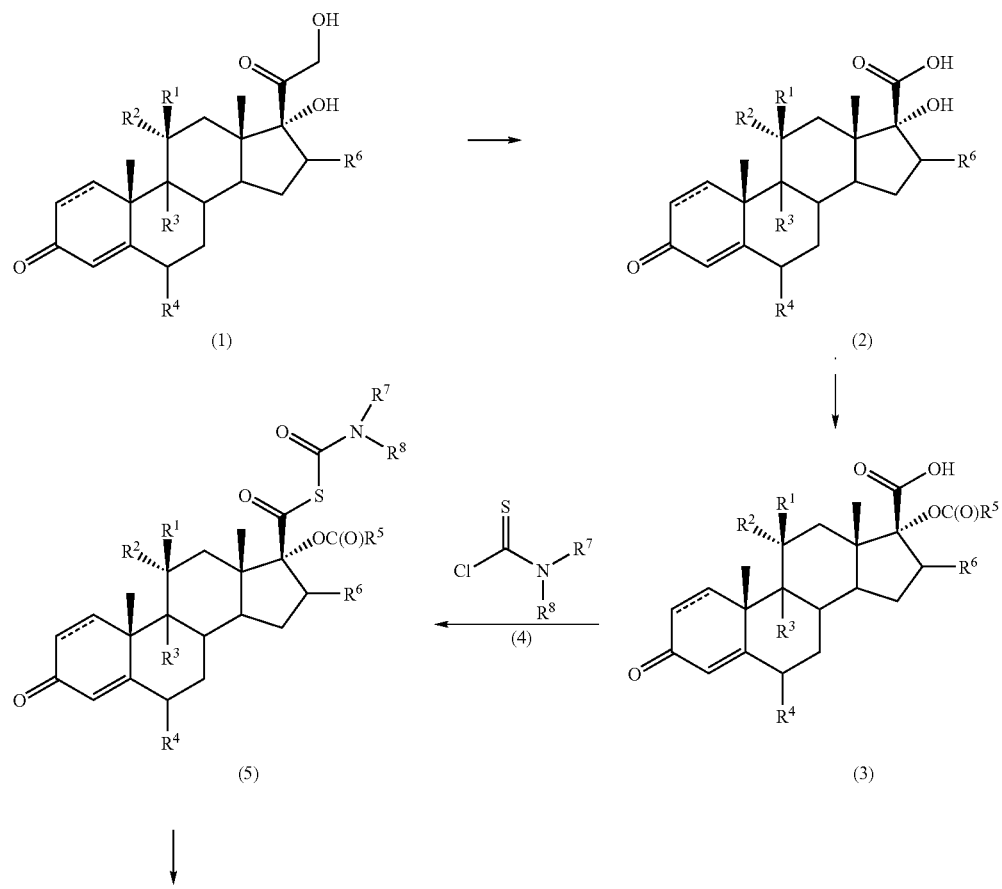

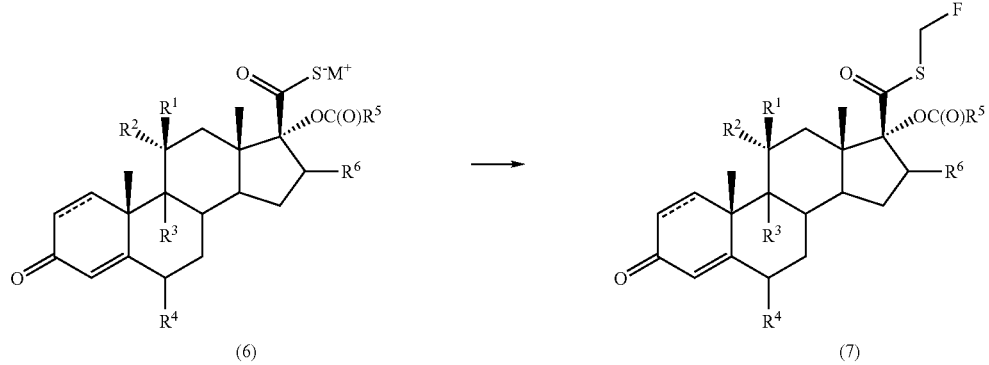

In one embodiment or Scheme 1, conversion of compounds of formula (1) to compounds of formula (2) can be achieved by reaction of the former and an oxidizing agent acid in a solvent such as $C_1$–$C_4$ alcohols, THF, dioxane, mixtures thereof, and mixtures of these solvents with water. Although the reaction generally proceeds at room temperature, it can be run at lower or higher temperatures, as needed. The reaction time is generally about 1 hour to about 18 hours and can be selected depending on the types of starting materials and the reaction temperature. In a preferred embodiment, this conversion is achieved by reaction of compounds of formula (1) in a THF/water mixture and periodic acid at about 0° C. to about 5° C. for about 3 hours.

The conversion of compounds of formula (2) to compounds of formula (3) can be achieved by reaction of the former and an alkanoyl halide in a solvent such as pyridine, diisopropylethylamine, triethylamine, THF, dioxane, benzene, toluene, diethyl ether, $C_2$–$C_5$ alkylamides, $C_3$–$C_{20}$ ketones, or mixtures thereof. Since acid is liberated with the progress of the reaction, it is preferable to run the reaction with at least a stoichiometric amount of base such as diisopropylethylamine, pyridine, or triethylamine. Although the reaction generally proceeds at lower temperature, it can be run at room temperature, as needed. The reaction time is generally about 30 minutes to about 5 hours and can be selected depending on the types of starting materials and the reaction temperature. In a preferred embodiment, this conversion is achieved by reaction of compounds of formula (3) in acetone and triethylamine at about –10° C. to about 0° C. and an alkanoyl chloride for about 30 minutes.

The conversion of compounds of formula (3) to compounds of formula (5) can be achieved by reaction of the former and compounds of formula (4) and an iodide salt such as an alkali metal iodide, an alkali earth metal iodide, or a tetraalkylammonium iodide in solvents such as water, $C_2$–$C_5$ alkylamides, $C_4$–$C_6$ dialkoxyalkyls, $C_1$–$C_4$ alcohols, $C_1$–$C_4$ haloalkyls, $C_3$–$C_{10}$ ketones, or mixtures thereof. Since acid is liberated with the progress of the reaction, it is preferable to run the reaction with at least a stoichiometric amount of a first base such as diisopropylethylamine, pyridine, or triethylamine. Compounds of formula (4) are available commercially or can be prepared by means well known in the art (*Tetrahedron*, 1980, 36(4), 539; Chem. Ber. 1980, 113(5), 1898; and *Justus Liebigs Ann. Chem.*, 1954, 590, 123). The reaction generally proceeds at about 0° C. to about 30° C. for about 1 hour to about 48 hours, depending on the reaction temperature and the nature of the reactants. In a preferred embodiment, this conversion is achieved by reaction of compounds of formula (3) and compounds of formula (4), triethylamine, and sodium iodide in 2-butanone and water, the water present in about one quarter percent by weight to about ten percent by weight of the compound of formula (3), for about 24 hours.

The conversion of compounds of formula (5) to compounds of formula (6) can be achieved by reaction of the former and a hydrolyzing agent such as an alkoxide salt, a thioalkoxide salt, an optionally hydrated sulfide salt, or a mixture thereof in solvents such as water, $C_2$–$C_5$ alkylamides, $C_4$–$C_6$ dialkoxyalkyls, $C_3$–$C_{10}$ ketones, or mixtures thereof. The reaction generally proceeds at about –40° C. to about 35° C. for about 1 hour to about 12 hours, depending on the reaction temperature and the nature of the reactants. In a preferred embodiment, this conversion is achieved by reaction of compounds of formula (5) and sodium hydrosulfide hydrate in DMA at about 0° C. to about 5° C. for about 2 hours then at room temperature for about 2 hours. The carbothioic acid salt thus formed can be acidified with an acid such as hydrochloric, hydrobromic, sulfuric, sulfonic, phosphoric, or trifluoroacetic or used directly in the next step without acidification.

The conversion of compounds of formula (6) to compounds of formula (7) can be achieved by reaction of the former and chlorofluoromethane in a $C_2$–$C_5$ alkylamide solvent such as DMF or DMA. The reaction generally proceeds at about –20° C. to about 30° C. for about 1 hour to about 12 hours, depending on the reaction temperature and the nature of the reactants. If the carbothioic acid salt has been acidified, then acid will be liberated during the course of the conversion, and the reaction is run in the presence of a second base such as sodium bicarbonate, potassium bicarbonate, sodium carbonate, or potassium carbonate. If the carbothioic acid salt has not been acidified, then the compounds of formula (6) can be reacted with chlorofluoromethane without isolation or purification. In a preferred embodiment, this conversion is achieved as a continuous process by in situ reaction of compounds of formula (6) and chlorofluoromethane as a solution in DMA at about 0° C. for about 3 hours then at room temperature and atmospheric pressure for about 12 hours.

In one embodiment of Scheme 1, the compound of formula (1) is commercial grade flumethasone; the compound of formula (2) is 6α,9α-difluoro-11β, 17α-dihydroxy-16α-methyl-3-oxoandrosta-1,4-diene-17β-carboxylic acid; the compound of formula (3) is 6α,9α-difluoro-11β-hydroxy-16α-methyl-3-oxo-17α-(propionyloxy)androsta-1,4-diene-17β-carboxylic acid; the compound of formula (5)

is 17β-(N,N-(dimethylcarbamoyl)thio)carbonyl-6α,9α-difluoro-11β-hydroxy-16α-methyl-17α-propionyloxy-3-oxoandrosta-1,4-diene; and the compound of formula (7) is 6α,9α-difluoro-17α-(((fluoromethyl)sulfanyl)-carbonyl)-11β-hydroxy-16α-methyl-3-oxoandrosta-1,4-dien-17α-yl propionate. Any one of these compounds can be reacted with a palladium catalyst and an additive, optionally in the presence of a reducing agent, in a solvent such as a $C_2$–$C_5$ alkylamide, a $C_4$–$C_6$ dialkoxyalkyl, an optionally substituted aromatic hydrocarbon, a $C_1$–$C_4$ haloalkyl a $C_3$–$C_{10}$ ketone, or a mixture thereof, to facilitate the removal the Cl impurity introduced by the commercial grade flumethasone. The palladium catalyst includes optionally supported palladium such as palladium metal, palladium metal on carbon, and palladium metal on acidic, basic, or neutral alumina; palladium(0) complexes such as tetrakis(triphenylphosphine)palladium(0); palladium salts such as palladium(II) acetate or palladium(II) chloride; and palladium(II) complexes such as allylpalladium(II) chloride dimer, (1,1'-bis(diphenylphosphino)ferrocene)-dichloropalladium(II), bis(acetato)bis(triphenylphosphine)palladium(II), and bis(acetonitrile)dichloropalladium(II). Additives useful for this reaction include tri(alkyl)phosphines such as trimethylphosphine, triethylphosphine, tributylphosphine, and the like; tri(cycloalkyl)phosphines such as tricyclopropylphosphine, tricyclohexylphosphine, and the like; tri(aryl)phosphines such as triphenylphosphine, trinaphthylphosphine, and the like; tri(heteroaryl)phosphines such as tri(fury-2-yl)phosphine, tri(pyrid-3-yl)phosphine, and the like; tri(alkyl)phosphites such as trimethylphosphite, triethylphosphite, tributylphosphite, and the like; tri(cycloalkyl)-phosphites such as tricyclopropylphosphite, tricyclohexylphosphite, and the like; tri(aryl)phosphites such as triphenylphosphite, trinaphthylphosphite, and the like; and tri(heteroaryl)phosphites such as tri(fury-2-yl)phosphite, tri(pyrid-3-yl)phosphite, and the like. Other additives useful for this reaction include bidentate phosphines such as 1,4-bis(diphenylphosphino)butane (dppb), 1,2-bis(diphenyl-phosphino)ethane (dppe), 1,1-bis(diphenylphosphino)methane (dppm), 1,2-bis(dimethylphosphino)ethane (dmpe), 1,1'-bis(diphenylphosphino)ferrocene (dppf), and the like. Reducing agents useful for this reaction include boranes such as diborane, 9-borabicyclo[3.3.1]nonane (9-BBN), dilongifoylborane, thexylborane, catecholborane, sodium borohydride, tetrabutylammonium borohydride, borane-4-methylmorpholine complex, borane-4-ethylmorpholine complex, borane-dimethylsulfide complex, borane-triethylamine complex, borane-pyridine complex, borane-2,6-lutidine complex, and the like; silanes such as diethylsilane, dimethylisopropylsilane, tributylsilane, cyclohexyldimethylsilane, diisopropyloctylsilane, triisopropylsilane, dimethylethylsilane, dimethyloctadecylsilane, triethylsilane, and the like; and stannanes such as diethylstannane, dimethylisopropylstannane, tributylstannane, cyclohexyldimethylstannane, diisopropyloctylstannane, triisopropylstannane, dimethylethylstannane, dimethyloctadecylstannane, triethylstannane, and the like. The reaction generally proceeds at about 0° C. to about 100° C. for about 10 minutes to about 12 hours, depending on the reaction temperature and whether the reducing agent is employed.

A summary of the reaction conditions useful for removing the Cl impurity from flumethasone is described in Table 1, Table 2, and Table 3. The initial % Cl impurity (mole % (before)) in the commercial grade flumethasone used for each of the reactions described in Table 1, Table 2, and Table 3 was determined to be about 0.7. The mole % Cl impurity (after) in the commercial grade flumethasone was then determined after treatment with the catalyst and the additive in the presence of a reducing agent. The mole percentages (mole %) of catalyst, additive, and reducing agent were calculated based on the moles of commercial grade flumethasone containing the 0.7 mole % Cl impurity. For example: 1 mole % palladium catalyst is 1 mole of palladium catalyst per 100 moles of commercial grade flumethasone; 2 mole % of additive is 2 moles of additive per 100 moles of commercial grade flumethasone; 20 mole % of reducing agent is 20 moles of reducing agent per 100 moles of commercial grade flumethasone; and so forth.

TABLE 1

| Additive | % Cl impurity (after) |
|---|---|
| [1]P(OPh)$_3$ | 0.48 |
| [1]P(furyl)$_3$ | 0.23 |
| [1]P(CH$_3$)$_3$ | 0.05 |
| [1]1,2-dppe | 0.47 |
| [1]1,4-dppb | 0.28 |
| [1]P(o-tol)$_3$ | 0.49 |
| [1]P(c-hex)$_3$ | 0.05 |
| [1]dppm | 0.10 |
| [1]1,3-dppp | 0.48 |
| [1]dppf | 0.31 |
| [1]P(Ph)$_3$ | 0.05 |
| [2]dppf | 0.16 |

[1]Reaction was conducted using 1 mole % palladium(II) acetate, 2 mole % monodentate additive or 1 mole % bidentate additive and 26 mole % triethylsilane in DMF at 22° C.
[2]Reaction was conducted using 1 mole % palladium(II) chloride, 2 mole % monodentate additive or 1 mole % bidentate additive and 26 mole % triethylsilane in DMF at 22° C.

TABLE 2

| mole % Pd | mole % P(Ph)$_3$ | mole % Et$_3$SiH | % Cl impurity (after) |
|---|---|---|---|
| 0.3 | 0.6 | 13 | 0.63 |
| 0.6 | 1.2 | 13 | 0.26 |
| 1 | 2 | 2.6 | 0.48 |
| 1 | 2 | 5 | 0.44 |
| 1 | 2 | 10 | 0.22 |
| 1 | 2 | 13 | 0.12 |
| 1 | 2 | 19 | 0.04 |

Reactions were conducted in DMA at 22° C.

TABLE 3

| mole % Pd | mole % P(Ph)$_3$ | mole % Et$_3$SiH | % Cl impurity (after) |
|---|---|---|---|
| 0.3 | 0.6 | 13 | 0.55 |
| 0.3 | 0.6 | 26 | 0.22 |
| 0.6 | 1.2 | 13 | 0.42 |
| 0.6 | 1.2 | 26 | 0.22 |
| 1 | 2 | 2.6 | 0.24* |
| 1 | 2 | 5 | 0.03* |
| 1 | 2 | 10 | 0.03 |
| 1 | 2 | 13 | 0.02 |

Reactions were conducted in DMF at 22 °C.
*Estimated value due to overlap of the Cl impurity with an unknown impurity.

In a preferred embodiment of the invention, the palladium catalyst is present in about 0.3 mol % to about 5 mol % of commercial grade flumethasone; the additive can be present in about 0.8 mol % to about 15 mol % of commercial grade flumethasone; and the reducing agent can be present in about 1 mol % to about 30 mol % of commercial grade flumethasone.

In one particularly preferred embodiment of the invention, palladium(II) acetate is present in about 1 mol % of commercial grade flumethasone; triphenylphosphine is present in about 2 mol % of commercial grade flumethasone; and triethylsilane is present in about 13 mol % of commercial grade flumethasone.

The invention will now be described in connection with other particularly preferred embodiments of Scheme 1, which are not intended to limit its scope. On the contrary, the invention covers all alternatives, modifications, and equivalents which are included within the scope of the claims. Thus, the following examples will illustrate an especially preferred practice of the invention, it being understood that the examples are for the purposes of illustration of certain preferred embodiments and are presented to provide what is believed to be the most useful and readily understood description of its procedures and conceptual aspects.

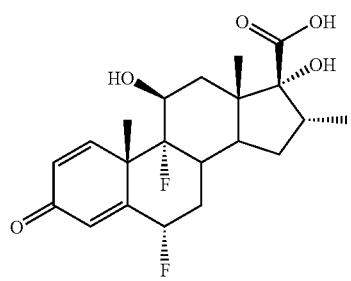

EXAMPLE 1

6α,9α-difluoro-11β,17α-dihydroxy-16α-methyl-3-oxoandrosta-1,4-diene-17β-carboxylic acid A mixture of commercial grade Flumethasone (100 g, 243.6 mmoles), palladium(II) acetate (0.552 g, 2.46 mmol) and triphenylphosphine (1.284 g, 4.89 mmol) in DMA (500 mL) at 60° C. was stirred for 30 minutes; cooled to 15° C. and treated with water (2.0 L) over 1 hour; cooled to 0° C., stirred for 2 hours, and filtered to provide a solid. The solid was washed with cold water (2×200 mL) and dissolved in THF (500 mL). This solution was cooled to 0° C., treated with technical grade (approximately 98%) periodic acid (83.3 g, 365.4 mmol) in water (250 mL), stirred for 3 hours, and treated with water (3.75 L); warmed to room temperature, stirred for 30 minutes, and filtered to provide a solid. This solid was washed with water (500 mL) until the pH of the wash was greater than 5 and dried under vacuum at 60° C. with a nitrogen purge to provide 96.6 g (98%) of the desired product.

EXAMPLE 2

6α,9α-difluoro-11β-hydroxy-16α-methyl-3-oxo-17α-(propionyloxy)androsta-1,4-diene-17β-carboxylic acid A solution of Example 1 (95.2 g, 240 mmol) and triethylamine (55.9 g, 552 mmol) in acetone (1.45 L) at −15° C. was treated with pre-distilled propionyl chloride (51.1 g, 552 mmol), stirred for 1 hour, treated with diethylamine (52.7 g, 720 mmol), stirred for 1 hour, and treated with 1M HCl (1.90 L); warmed to 0° C., stirred for 1 hour, and filtered. The solid was washed with water (475 mL), dried for 12 hours at 60° C. under vacuum with a nitrogen purge, and treated sequentially with 3-pentanone (459 mL), 2-butanone (51 mL), and water (5.1 mL). This mixture was heated to reflux for one hour; cooled to room temperature over two hours, stirred for 18 hours, and filtered to provide a solid. This solid was washed with 3-pentanone (100 mL) and dried under vacuum with a nitrogen purge at 60° C. for 18 hours to provide 86.7 g (79.8%) of the desired product.

EXAMPLE 3

17β-(N,N-(dimethylcarbamoyl)thio)carbonyl-6α,9α-difluoro-11β-hydroxy-16α-methyl-17α-propionyloxy-3-oxoandrosta-1,4-diene A solution of Example 2 (86.7 g, 192 mmol) and N,N-dimethylthiocarbamoyl chloride (47.5 g, 384 mmoles) in 2-butanone (2.17 L) at room temperature was treated sequentially with triethylamine (42.7 g, 422 mmoles), anhydrous sodium iodide (28.8 g, 192 mmol), and water (8.67 mL, 10% w/w with Example 2), stirred for 2 hours, treated sequentially with DMA (694 mL) and water (4.34 L); cooled to 0° C., stirred for 2 hours, and filtered to provide a solid. The solid was washed with water (500 mL) and dried at 60° C. under vacuum with a nitrogen purge to provide 96.4 g (93%) of the desired product.

EXAMPLE 4

6α,9α-difluoro-17α-(((fluoromethyl)sulfanyl)carbonyl)-11β-hydroxy-16α-methyl-3-oxoandrosta-1,4-dien-17α-yl propionate (fluticasone propionate)

A solution of Example 3 (96.4 g, 179 mmol) and sodium hydrosulfide hydrate (45.3 g, 808 mmol) in dimethylacetamide (386 mL) at 0° C. was stirred for 2 hours; warmed to room temperature and stirred for 2 hours; cooled to −5° C., treated slowly with a solution of chlorofluoromethane (92.7 g, 1.354 mol) in dimethylacetamide (313 mL), and stirred for 4 hours; warmed to room temperature, stirred for 18 hours and treated slowly with a solution of sodium bicarbonate (29.9 g) in water (1.45 L); cooled to −5° C., stirred for two hours, and filtered to provide a solid. The solid was washed sequentially with water (145 mL) and 1-butanol (145 mL) and treated with ethyl acetate (540 mL) and 1-butanol (2.16 L) to provide a mixture. The mixture was heated to reflux for 40 minutes and filtered hot (without rinsing) through a less than 1 micron filter. The filtrate was stirred while cooling to room temperature, stirred for eight hours, and filtered to provide a solid. This solid was washed with 1-butanol, (145 mL), recrystallized from 1-butanol (2.70 L), and dried under vacuum with a nitrogen purge at 60° C. to provide 62.7 g (70%) of the desired product.

EXAMPLE 5

17β, (N,N-(dimethylcarbamoyl)thio)carbonyl-6α, 9α-difluoro-11β-hydroxy-16α-methyl-17α-acetyloxy-3-oxoandrosta-1,4-diene A solution of 6α,9α-difluoro-11β-hydroxy-16α-methyl-3-oxo-17α-(acetyloxy)androsta-1,4-diene-17β-carboxylic acid (4.85 g, 11.1 mmol), N,N-dimethylthiocarbamoyl chloride (2.73 g, 22.2 mmol) in 2-butanone (122 mL) at room temperature was treated sequentially with triethylamine (3.4 mL, 24.4 mmol), anhydrous sodium iodide (1.67 g, 11.1 mmol), and water (0.5 mL, 10% w/w with the carboxylic acid), stirred for 12 hours, treated sequentially with DMA (40 mL) and water (242 mL); cooled to 0° C., stirred for 1 hour, and filtered to provide a solid. The solid was washed with water and dried at 60° C. under vacuum with a nitrogen purge to provide 5.81 g (90%) of the desired product.

EXAMPLE 6

6α,9α-difluoro-11β-hydroxy-17α-(acetylyloxy)-16α-methyl-3-oxoandrostat-1,4-diene-17β-thiocarboxylic acid A solution of Example 5 (5.0 g, 9.51 mmol) in DMA (50 mL) at −15° C. was treated with sodium thiomethoxide (0.73 g, 10.46 mmol) in one portion, and stirred for 4.5 hours; warmed to 0° C., treated with cold 1M HCl (100 mL), stirred for 1 hour, and filtered. The solid was washed with water until the wash was pH 6 or higher and dried under vacuum at 60° C. with a nitrogen purge to provide 4.32 g, (93%) of the desired product.

EXAMPLE 7

17β-((N,N-dimethylcarbamoyl)thiocarbonyl)-9α-fluoro-11β-hydroxy-17α-(propionyloxy)-16α-methyl androstat-1,4-diene-3-one A solution of 9α-fluoro-11β-hydroxy-17α-(propionyloxy)-16α-methyl-3-oxoandrostat-1,4-diene-17β-carboxylic acid (10.0 g, 23.04 mmol) and N,N-dimethylthiocarbamoyl chloride (5.67 g, 46.08 mmol) in dichloromethane (130 mL) at room temperature was treated sequentially with triethylamine (6.5 mL, 46.08 mmol) and anhydrous sodium iodide (3.45 g, 23.04 mmol), stirred for 12 hours, and filtered through diatomaceous earth (Celite®) with dichloromethane (25 mL). The filtrate was concentrated under reduced pressure. The concentrate was treated sequentially with DMA (150 mL) and water (190 mL); cooled to 0° C., and stirred for 1 hour. The resulting solid was collected by filtration, washed with water, and dried under vacuum at 60° C. with a nitrogen purge to provide 10.2 g, (85%) of the desired product.

EXAMPLE 8

9α-fluoro-11β-hydroxy-17α-(propionyloxy)-16α-methyl-3-oxoandrostat-1,4-diene-17β-thiocarboxylic acid A solution of Example 7 (5.0 g, 9.58 mmol) in DMA (50 mL) at −15° C. was treated with sodium thiomethoxide (0.74 g, 10.54 mmol) in one portion, stirred for 2 hours; warmed to 0° C., treated with cold 1M HCl (100 mL), stirred for 1 hour at 0° C., and filtered. The resulting solid was washed with water until the wash was pH 6 or higher and dried under vacuum at 60° C. with a nitrogen purge to provide 4.10 g, (95%) of the desired product.

It will be evident to one skilled in the art that this invention is not limited to the forgoing examples, and that it can be embodied in other specific forms without departing from the essential attributes thereof. Thus, it is desired that the examples be considered as illustrative and not restrictive, reference being made to the claims, and that all changes which come within the meaning and range of equivalency of the claims be embraced therein.

What is claimed is:

1. A method for the preparation of a compound of formula (7)

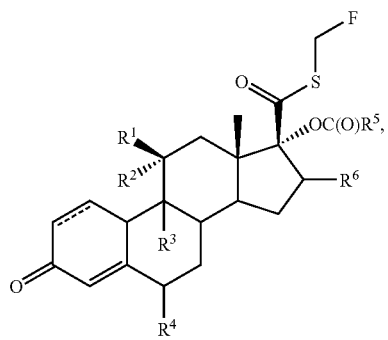

wherein the symbol ═══
represents a single bond or a double bond; one of $R^1$ or $R^2$ is hydrogen and the other is optionally protected hydroxyl; or $R^1$ and $R^2$ together are oxo; $R^3$ and $R^4$ are independently hydrogen or halide; and $R^5$ and $R^6$ are independently $C_1$–$C_6$ alkyl; the method comprising:

(c) reacting a compound of formula (3)

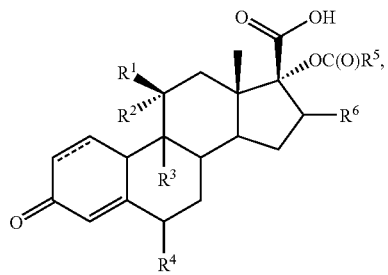

and a first base, an iodide salt, and the compound of formula (4)

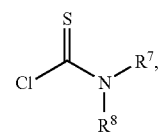

wherein $R^7$ and $R^8$ are independently $C_1$–$C_6$ alkyl; or $R^7$ and $R^8$ together are $C_1$–$C_6$ alkaline, in a solvent comprising 2-butanone and water, the water present in about one quarter percent by weight to about ten percent by weight of the compound of formula (3)

to provide a compound of formula (5)

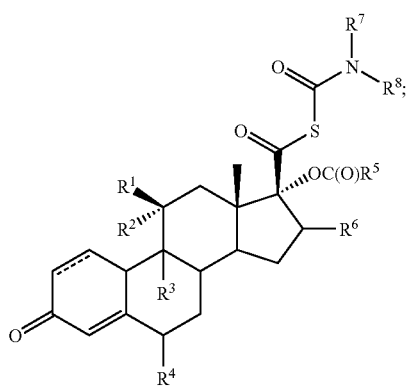

(d) reacting the product of step (c) and NaSH to provide a compound of formula (6)

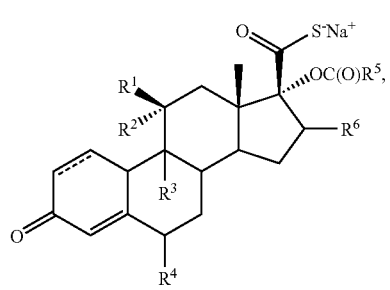

(e) reacting the product of step (d) and acid;
(f) reacting the product of step (e) and chlorofluoromethane optionally in the presence of a second base; and
(g) optionally deprotecting the product of step (f).

2. The method of claim 1, wherein the first base is a carbonate salt, an amine, or a mixture thereof.

3. The method of claim 1, wherein the iodide salt is an alkali metal iodide, an alkali earth metal iodide, or a tetraalkylammonium iodide.

4. The method of claim 1, wherein the second base is a carbonate salt.

5. A method for the preparation of a compound of formula (7)

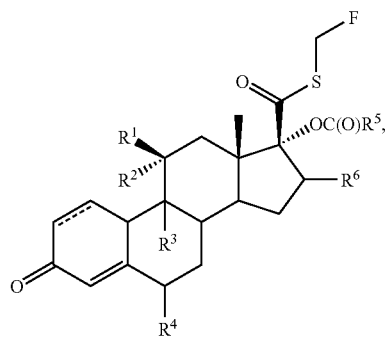

wherein the symbol ≡≡≡ represents a single bond or a double bond; one of $R^1$ or $R^2$ is hydrogen and the other is optionally protected hydroxyl; or $R^1$ and $R^2$ together are oxo; $R^3$ and $R^4$ are independently hydrogen or halide; and $R^5$ and $R^6$ are independently $C_1$–$C_6$ alkyl; the method comprising:

(b) reacting a compound of formula (2)

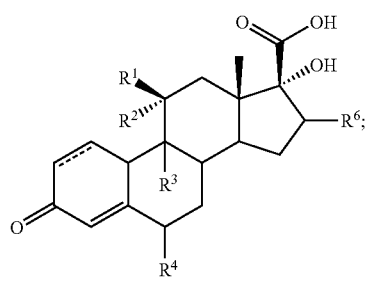

and an alkanoyl halide and the first base to provide the compound of formula (3)

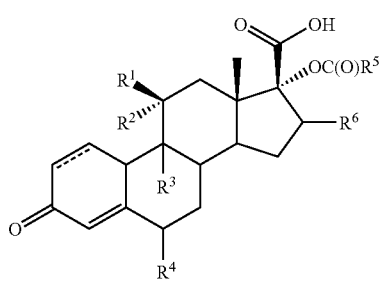

(c) reacting a compound of formula (3)

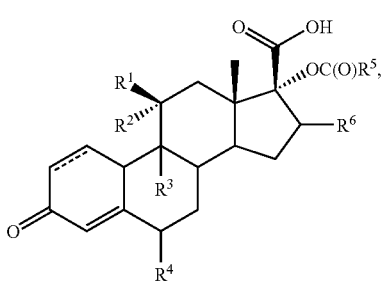

and a first base, an iodide salt, and a compound of formula (4)

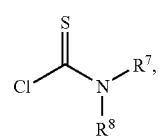

wherein $R^7$ and $R^8$ are independently $C_1$–$C_6$ alkyl; or $R^7$ and $R^8$ together are $C_1$–$C_6$ alkaline, in a solvent comprising 2-butanone and water, the water present in about one quarter percent by weight to about ten percent by weight of the compound of formula (3) to provide a compound of formula (5)

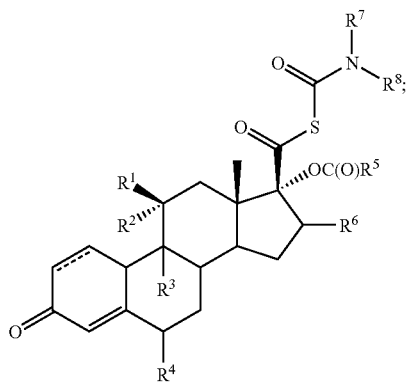

(d) reacting the product of step (c) and NaSH to provide a compound of formula (6)

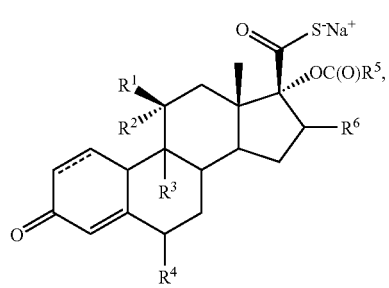

(e) reacting the product of step (d) and acid;
(f) reacting the product of step (e) and chlorofluoromethane optionally in the presence of a second base; and
(g) optionally deprotecting the product of step (f).

6. A method for the preparation of a compound of formula (7)

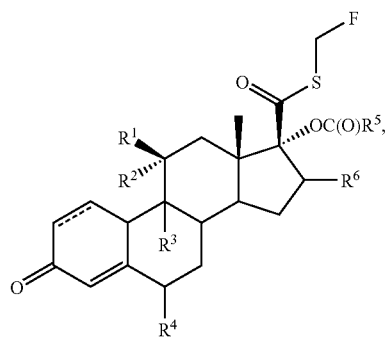

wherein the symbol ==== represents a single bond or a double bond; one of $R^1$ or $R^2$ is hydrogen and the other is optionally protected hydroxyl; or $R^1$ and $R^2$ together are oxo; $R^3$ and $R^4$ are independently hydrogen or halide; and $R^5$ and $R^6$ are independently $C_1$–$C_6$ alkyl; the method comprising:

(c) reacting a compound of formula (3)

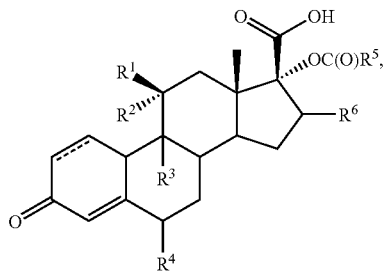

and a first base, an iodide salt, and the compound of formula (4)

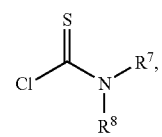

wherein $R^7$ and $R^8$ are independently $C_1$–$C_6$ alkyl; or $R^7$ and $R^8$ together are $C_1$–$C_6$ alkaline, in a solvent comprising 2-butanone and water, the water present in about one quarter percent by weight to about ten percent by weight of the compound of formula (3) to provide a compound of formula (5)

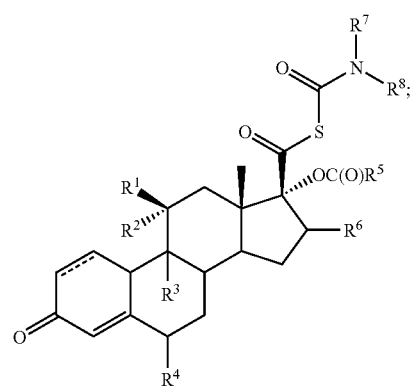

(d) reacting the product of step (c) and NaSH to provide a compound of formula (6)

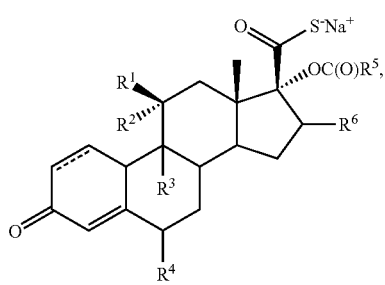

(e) reacting the product of step (d) and chlorofluoromethane; and
(f) optionally deprotecting the product of step (e).

7. A method for the preparation of a compound of formula (7)

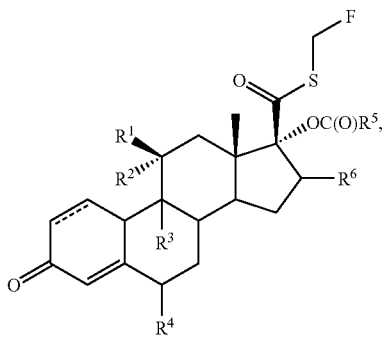

wherein the symbol ════ represents a single bond or a double bond; one of $R^1$ or $R^2$ is hydrogen and the other is optionally protected hydroxyl; or $R^1$ and $R^2$ together are oxo; $R^3$ and $R^4$ are independently hydrogen or halide; and $R^5$ and $R^6$ are independently $C_1$–$C_6$ alkyl; the method comprising:

(b) reacting a compound of formula (2)

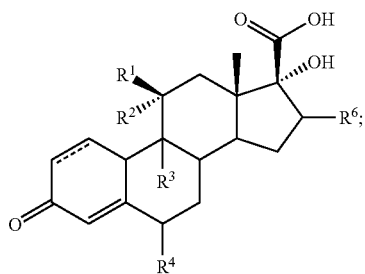

and an alkanoyl halide and the first base to provide the compound of formula (3)

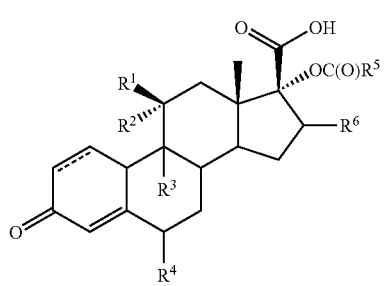

(c) reading a compound of formula (3)

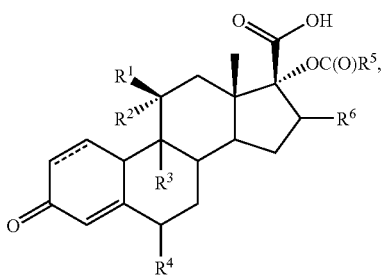

and a first base, an iodide salt, and a compound of formula (4)

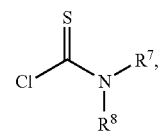

wherein $R^7$ and $R^8$ are independently $C_1$–$C_6$ alkyl; or $R^7$ and $R^8$ together are $C_1$–$C_6$ alkaline, in a solvent comprising 2-butanone and water, the water present in about one quarter percent by weight to about ten percent by weight of the compound of formula (3) to provide a compound of formula (5)

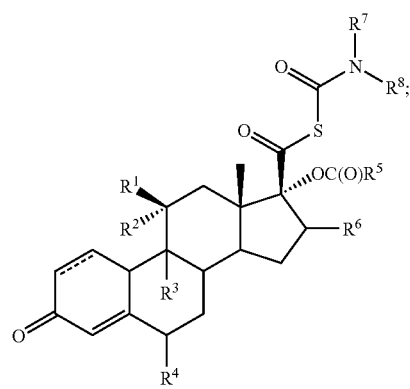

(d) reacting the product of step (c) and NaSH to provide a compound of formula (6)

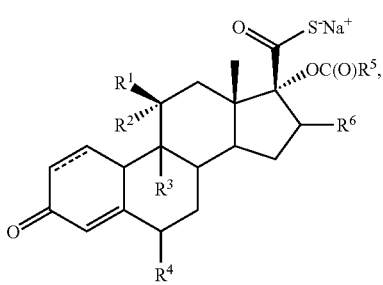

(e) reacting the product of step (d) and chlorofluoromethane; and
(f) optionally deprotecting the product of step (e).

* * * * *